US005254283A

United States Patent [19]

Arnold et al.

[11] Patent Number: 5,254,283

[45] Date of Patent: Oct. 19, 1993

[54] ISOPHTHALIC POLYMER COATED PARTICLES

[75] Inventors: Raymond E. Arnold, San Francisco; Nathaniel T. Becker, Burlingame, both of Calif.

[73] Assignees: Genencor International, Inc.; Eastman Kodak Co., both of Rochester, N.Y.

[21] Appl. No.: 642,596

[22] Filed: Jan. 17, 1991

[51] Int. Cl.[5] .................... C11D 3/386; C11D 3/37; C12N 9/99

[52] U.S. Cl. .................... 252/174.12; 252/174.13; 252/DIG. 2; 252/DIG. 12; 435/180; 435/187; 435/188; 427/213

[58] Field of Search .................... 252/174.12, 174.13, 252/174.23, DIG. 2, DIG. 12; 435/188, 180, 187; 427/213

[56] References Cited

U.S. PATENT DOCUMENTS

| | | | |
|---|---|---|---|
| 3,992,558 | 11/1976 | Smith-Johannsen et al. | 427/213 |
| 4,090,973 | 5/1978 | Maguire, Jr. et al. | 252/89 |
| 4,548,727 | 10/1985 | Shaer | 252/171 |
| 4,671,972 | 6/1987 | Schobel et al. | 427/213 |
| 4,689,297 | 8/1987 | Good et al. | 435/174 |
| 4,722,865 | 2/1988 | Huizer | 428/407 |
| 4,759,956 | 7/1988 | Amer et al. | 427/213 |
| 4,762,637 | 8/1988 | Aronson et al. | 252/99 |
| 4,965,012 | 10/1990 | Olson | 252/174.12 |
| 4,973,417 | 11/1990 | Falholt | 252/95 |
| 5,093,021 | 3/1992 | Coyne et al. | 252/91 |
| 5,133,892 | 6/1992 | Chun et al. | 252/90 |
| 5,167,854 | 1/1992 | Deleeuw et al. | 252/186.27 |

OTHER PUBLICATIONS

"Process For Suppression of Coal Dust", Res. Discl., 276, 237, 1987.

*Primary Examiner*—Paul Lieberman
*Assistant Examiner*—Kery A. Fries
*Attorney, Agent, or Firm*—Margaret A. Horn

[57] ABSTRACT

The invention relates to use of a water dispersible isophthalic acid polymer as a dust free coating on particulates. The particles provide a timed release of the contents of the particle which allows for reduced amounts of active agents on the coatings and less interference between active agents in the coating or environment and the particulates.

8 Claims, 1 Drawing Sheet

Figure 1. Protease and Ammonium Sulfate Release

Detergent Solution at 95 F in a Dissolution Tester

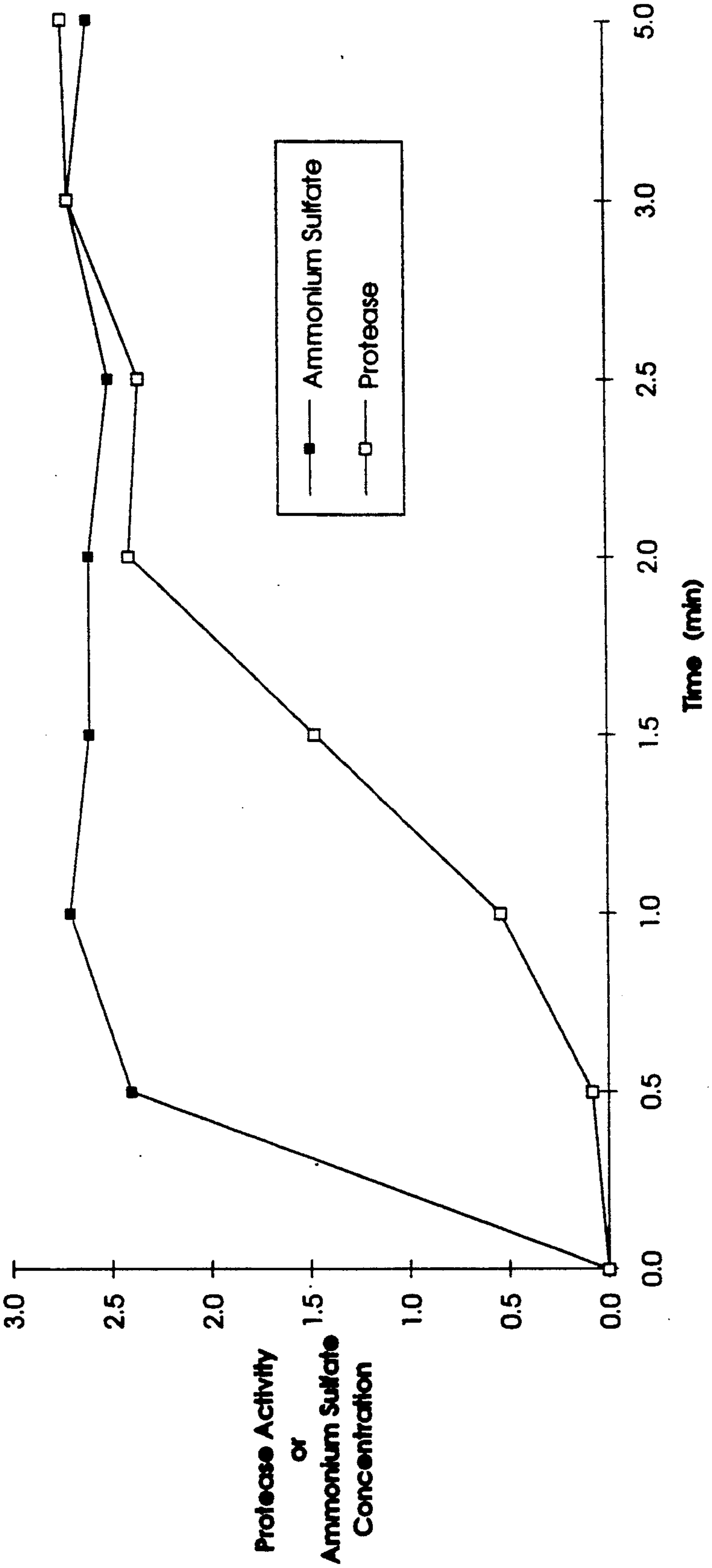
Figure 1. Protease and Ammonium Sulfate Release
Detergent Solution at 95 F in a Dissolution Tester

ISOPHTHALIC POLYMER COATED PARTICLES

FIELD OF THE INVENTION

The invention relates to dried dust free particles. In particular the invention relates to particles which have been coated with a water dispersible coating of an isophthalic acid polymer. The particles are particularly useful for use as a coating with laundry detergent granules.

BACKGROUND OF THE INVENTION

When formulating dried particulate products such as would be made in a fluid bed dryer (e.g. particles for use in washing compositions), two problems normally occur. The first problem is that of dusting. The method of manufacturing particles can create very fine powders which cause dermatologic effects when the product contains sensitizing agents (e.g. enzymes in a detergent granule). The second problem relates to the need to incorporate relatively high amounts of ingredients such as enzyme protecting agents, masking agents and scavengers (e.g. chlorine scavengers) into products for the purpose of binding ions which can inactivate an active ingredient in the particle. It would be desirable to use less of these types of materials or to use them without interfering with enzymes that may be present.

Many commercially useful enzymes are produced by microorganisms, particularly bacteria, yeast and filamentous fungi. These enzymes are especially useful in detergent and food applications. With the advent of biotechnology and recombinant DNA techniques, other enzymes from mammlian sources are produced recombinantly in microorganisms. When enzymes are produced in a microbial host they are usually either secreted directly into the fermentation both by the microorganism or released into the fermentation broth by lysing the cell. The enzyme can then be recovered from the broth in a soluble form by a number of techniques including filtration, centrifugation, membrane filtration, chromatography and the like. The dissolved enzyme can be converted to a dry form from a liquid using techniques such a precipitation, crystallization or spray-drying. A problem associated with dry enzyme preparations is that there is a high dust level associated with them, which can cause dermatologic distress to the manufacturer, consumer or any other person handling the enzyme. It has been a desire in the art to treat these dry enzymes so as to reduce the hazard of dusting. To control dusting and increase particle size, dry enzymes are often granulated by various means known by those skilled in the art.

Various enzyme formulations and processes for these preparations have been developed in an effort to alleviate the dusting problem. For example, German Patent No. 21 37 042 discloses a process in which an enzyme-containing formulation is extruded through a die onto the revolving plate of a spheronizing device to form sperical particles of the enzyme-containing formulations which are optionally coated with a material designed to prevent dusting.

In U.S. Pat. No. 4,087,368, there is disclosed an enzyme granule formulation in which rods or spheres of an enzyme in admixture with magnesium alkyl sulfate and ethylene oxide are provided.

U.S. Pat. No. 4,016,040 discloses a method for the preparation of free-flowing substantially dust-free, spherical enzyme-containing beads prepared by blending a powdered concentrate of the enzyme with a binder in molten form and spraying droplets of the blend through a spray nozzle into cool air to solidify the droplets and form the beads.

In U.S. Pat. No. 4,242,219, there is claimed a process for the preparation of enzyme-containing particles prepared by mixing the dry enzyme with a hydrophilic organic cohesive material, a building agent or a mixture regulating agent and mechanically dividing it into particles of the desired size and shape which are then coated with a water repellent material.

Another type of granular enzyme formulation is described in U.S. Pat. No. 4,009,076. This formulation is prepared by mixing the dry enzyme with a solid nonviable substance and optionally a cohesive organic material as binder to form an enzymatically active core. An enzyme slurry containing the cohesive organic material can be sprayed onto, for example, sodium tripolyphosphate in a mixer or an enzyme powder can be mixed with the sodium tripolyphosphate and the cohesive organic material sprayed onto it with subsequent extrusion through a die. The enzyme-containing granule is sprayed with an aqueous solution containing a plasticized organic resin, then dried.

A process is described in GDR Patent 0 151 598 in which sodium tripolyphosphate is sprayed with an aqueous fermentation broth and agglomerated in a cyclone apparatus. The agglomerates are removed from the cyclone apparatus while still wet and placed in a mechanical blender with a drying detergent formulation and intensively mixed.

In British Patent No. 1,483,591, there is described a process for coating water soluble or water dispersible particles, including enzyme particles, using a fluidized-bed reactor. This reference involves a dust-free coating technique for enzyme particles which have been granulated by other processes such as prilling or spheronizing.

In U.S. Pat. No. 4,689,297, there is described a method for preparing dust-free enzyme involving dissolving or suspending dry enzyme in solution to make a slurry of at least 30% w/w of the solids enzymes, spraying it on a hydratable core and then coating it with macromolecular material.

In PCT patent application 87/00057 there is described a detergent enzyme product with an enzyme core on which is an enteric coating. Such coatings are water soluble and dissolve readily at high pH's while resisting dissolution at low pH's.

Oxidant scavengers or enzyme protecting agents or masking agents can be included in washing compositions to bind free ions, compounds or the like, which may inactivate the enzyme or decrease its efficacy or otherwise interfere with the ability of the detergent or enzyme preparation.

It is desirable to produce improved dust free particles which can decrease or eliminate the need for scavengers, enzyme protecting agents, or masking agents and other such compounds or increase the effectiveness of enzymes in the presence of ions.

SUMMARY OF THE INVENTION

It has surprisingly been found that a dry dust-free particle can be produced which reduces the need for scavengers, protecting agents, or masking agents and/or improves the effectiveness of enzymes therein and additionally provides a particle with delayed dissolution times. The product comprises a particulate material to which has been applied a continuous layer of a non-water soluble isophthalic acid polymer or other warp size agent, preferably in the presence of a detergent. Particularly within the scope of this invention are enzyme and detergent particles prepared with a non-water soluble isophthalic acid polymer. In a preferred embodiment, a crosslinking agent consisting of a multivalent cation salt, such as aluminum sulfate, is incorporated into the particle.

DESCRIPTION OF THE FIGURE

FIG. 1 is a graphic representation showing the simultaneous release of ammonium sulfate and protease in solution prior to the release of the enzyme.

DETAILED DESCRIPTION OF THE INVENTION

"Warp size" as used herein refers to compositions, in this case isophthalic acid polymers, normally used in the textile industry. These agents are sprayed on thread during the weaving process to help protect them against damage (e.g. by abrasion). Normally the size material is removed by use of desizing agents prior to sale of the goods. Many such warp size agents are known to be readily dispersible in water, but not soluble, and such are ones suitable for the present invention. A preferred isophthalic acid polymer and warp size is available commercially as AQ-55 from Eastman Chemicals Co. but chemically is poly [82/18-isophthalic acid/S-sodiosulfoisophthalic acid-54/46 diethyleneglycol/1,4-cyclohexane dimethanol]. Other such agents are known in the prior art and/or could easily be synthesized. It has been discovered that where these agents are used to coat particles, they offer several advantages over the macromolecular films previously used to coat particles. They coat well, contain dust, and produce a nonfriable particle. They can be applied at high solids concentration from dispersions (typically 10–30% w/w solids, which entails reduced coating times), and are stable at high temperature and humidity. An important benefit of using these compounds is their ability to spread the release of the enzyme contents of the particle over about 1-3 minutes after addition to an aqueous detergent environment. This is useful when scavengers, protecting agents, etc., such as ammonium sulfate, are used which act to sequester or inactivate available chlorine or other oxidizing agents or components harmful to enzymes. Such enzyme protecting agents are disclosed in U.S. Ser. No. 07/642,619 now abandoned filed on even date with this application entitled "GRANULES CONTAINING BOTH AN ENZYME AND AN ENZYME PROTECTING AGENT AND DETERGENT COMPOSITIONS CONTAINING SUCH GRANULES". The delay in release allows the chlorine or other ions to be bound to available substrates other than the enzyme, prior to release of the enzyme, thus decreasing the need for scavengers, protecting agents, or masking agents. These other substrates, such as the proteinaceous stains on clothing and other amino or thiol compounds can often be present in the environment where enzyme granules might be used, such as a washing machine. Under some conditions the delay in release in itself may offer sufficient protection, and no added scavengers or protecting agents or masking agents may be needed. For example, in clothes washing detergent compositions the detergent and soiled clothing can be allowed to react with and bind the available chlorine after which the enzyme can be released in a more favorable environment eliminating or greatly reducing the need for a scavenger or protecting agent or masking agent.

The term "non-water soluble" means that upon contact with water, the polymer does not solubilize (as, for example, in an enteric coating). "Delayed release" means that at least a portion of the particulate material is released into the surrounding water over a period of time such that at least about 90% of the enzyme or other selected component of the particulate material coated with the non-water soluble coating is released within 7 minutes, more preferably within about 2–4 minutes, but not more than 50% is released within 30 seconds. Release of the enzyme and other components underneath the polymer coating may take place by either polymer erosion, dispersion or diffusion through the polymer (for example, when the polymer swells upon contact with water), or by a combination of these or other mechanisms. Time of release of the enzyme and other components can be further delayed by crosslinking the polymer. Crosslinking is carried out by incorporating multivalent cation salts, such as $Al_2(SO_4)_3$ or $MgSO_4$ beneath the polymer coating. Crosslinking may actually occur only once the granule is wetted. The degree of crosslinking will affect the rate of polymer erosion and enzyme release. These coatings are also effective in combination with powdered fillers such as $TiO_2$ or talc. Besides serving as cosmetic whiteners, these powdered fillers aid in preventing agglomeration during the coating process.

"Particulate material" refers to relatively small particles in the area of 150–1500 microns. In a preferred embodiment the particle is a spray-coated particle with a soluble or dispersible core to which a spray coating has been applied. In the case of a detergent particulate material (a preferred particle), such particle would contain a core of a soluble or dispersible solid such as non pareil salt crystals to which has applied to it detergent, enzyme, scavenger, protecting agent, etc. in one or more coats.

Coated particles of the present invention can be made in a fluidized-bed spray-coater. Typically, such devices comprise a fluidized-bed dryer consisting of a cylindrical product chamber that has a porous grid on the bottom and is open on the top to be put up against a conical shaped expansion chamber of a larger diameter than the cylindrical product chamber; a filter to collect dust and a fan to help air flow is placed at the far end of the expansion chamber and a spray nozzle is located within the chamber to apply the solution to the core material. In operation, as the velocity of air passing up through the chamber is increased, a point is reached where particles resting on the porous grid are suspended in the air flow as a fluid, hence the terms "fluidization" and "fluidized-bed dryer". The particles are lifted by the upward force of the air out of the product chamber into the expansion chamber where the air expands and the upward force per unit of area is reduced. This allows the particles to fall back into the product chamber and start the cycle over.

The initial step in the method involves introducing a particulate, core material into the reaction chamber of the fluidized-bed dryer and suspending the particles therein on a stream of air. The core particles preferably are composed of a highly hydratable material, i.e. a material which is readily dispersible or soluble in water. The core material should either disperse (fall apart by failure to maintain its integrity) or dissolve by going into a true solution. Clays (bentonite, kaolin), non pareils and agglomerated potato starch are considered dispersible. Non pareils are spherical particles consisting of a solid sugar core that has been built up and rounded into a spherical shape by binding layers of sugar, starch and possibly other materials to the core in a rotating spherical container and are preferred.

Salt particles (NaCl crystals, NaCl rock salt, $NaHCO_3$) are considered soluble particles useful in the invention. More particularly, core particles can be non pareils with or without a final coat of dextrin or a confectionery glaze. Also suitable are agglomerated trisodium citrate, pan crystallized NaCl flakes, bentonite granules and prills, bentonite/kaolin/diatomaceous earth disk-pelletized granules and sodium citrate crystals. The core particle is of a material which is not dissolved during the subsequent spraying process and is preferably of a particle size from 150 to 2,000 microns (100 mesh to 10 mesh on the U.S. Standard Sieve Series) in its longest dimension.

Enzymes and other agents, including any optional metallic salts, pigments, solubilizers, activators, antioxidants, dyes, inhibitors, binders, plasticizers, fragrances, etc. are applied to the surface of the particulate material by fluidizing the particles in a flow of air whereupon a broth containing the enzyme and other solutes or suspended material is then atomized and sprayed into the expansion chamber of the spray-coater. The atomized droplets contact the surface of the particles leaving a film of the solids adhering to the surface of the particles when the water and other volatiles are evaporated.

Airflow is maintained upwards and out the top of the expansion chamber through a filter. The filter may be located inside or outside of the unit, or may be substituted for by a scrubber or cyclone. This filter or scrubber or cyclone traps fine dried particles which contribute to dust. Fluidized-bed spray-coaters that have this filter typically have automatic shakers which shake the filter to prevent excessive restriction of the air flow.

When sufficient enzyme or other solids are applied to the core particles to provide the desired size particles, while still suspended in the reaction chamber of the coater or later reintroduced therein, the particles are coated with a layer of the isophthalic acid polymer of the invention with the scavenger or other desired ingredient and optional fillers. Optionally, a solution or suspension containing a crosslinking agent, typically a multivalent cation salt, can be sprayed onto the particulate material prior to applying the isophtalic acid polymer. (Actually, crosslinking may not occur until the particle is subsequently wetted and the crosslinking agent can diffuse into the polymer layer.) This is accomplished in a manner similar to that used for application of the enzyme/solids coating. The isophthalic acid polymer should be roughly 1–15% w/w of the entire particle and roughly 10–100% of the final coating.

The dust-free enzyme particles containing enzymes of the present invention can be used wherever enzymes or other agents are needed in a dry form. Thus, they can be used as additives to dry detergent formulations, for removing gelatin coatings on photographic films, to aid in silver recovery, in the digestion of wastes from food processing plants for nitrogen recovery, in denture cleansers for removing protein bound stains in food preparation, in textile applications such as desizing and a processing aid in waste water treatment. In general, they can be used anywhere it is desirable to delay the release of an enzyme or other agent.

The following outlines ingredients, other than enzymes, which could be present in the coated particulate material:

ENZYME PROTECTING AGENTS AND SCAVENGERS

The enzyme protecting agents employed herein refer to those compounds which, when incorporated in the granules at a sufficient concentration, will prevent significant loss of enzyme activity over time when these granules are added to a detergent wash medium. Suitable enzyme protecting agents include ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein, and the like, etc.

The concentration of the enzyme protecting agent employed in combination with the enzyme in the granule is an amount effective to retard the loss of enzymatic activity in the detergent wash medium, i.e., provide resistance to enzymatic activity degradation in the detergent wash medium. It is believed that oxidizing moieties in the detergent wash medium are responsible for oxidizing the amine, ammonium and sulhydryl functionalities of amine, ammonium and/or sulhydryl containing amino acids in the enzyme and that this oxidation accounts for at least part of the loss of enzymatic activity. It is further believed that enzyme protecting agents containing functional groups such as $-NH_3$, $-NH_4^+$, —SH and the like protect the enzyme from enzymatic activity degradation by offering alternative sites for oxidation by the oxidizing moieties. That is to say that the presence of a large number of these functionalities in the detergent wash medium will result in enzyme protection because, by sheer number of such functionalities, oxidizing agents present in the wash medium will preferentially oxidize these functionalities rather than oxidizing oxidizable functionalities on the enzyme. Accordingly, such functional groups are described herein as enzyme protecting functional groups.

It is believed that normally an initially very high concentration of the enzyme protecting agent in the microenvironment of the enzyme prevents any significant oxidation of the enzyme by those oxidizing groups found in the detergent wash medium. In contrast, if the enzyme and enzyme protecting agent are merely combined into the detergent composition as separate components, this high concentration of enzyme protection agent in the microenvironment of the enzyme cannot form and accordingly, significantly less protection is accorded to the enzyme. Whereas in the present invention, the coating allows for a reduction in the amount of protecting agent needed.

In view of the above, the concentration of the enzyme protecting agent necessary to impart protection to the enzyme in the detergent wash medium is related to the number of enzyme protecting functional groups present on the protecting agent molecule, and to the delay in release of enzyme, and to the agent being protected against.

In general, the concentration of the enzyme protecting agent employed is an amount effective to retard the loss of enzymatic activity of the enzyme in the wash medium. Preferably, the enzyme protecting agent is selected so as to provide at least about 1.0 micromols/-liter of the enzyme protecting functional groups in the detergent wash medium. More preferably, the concentration of the enzyme protecting agent is selected so as to provide at least about 5 micromols of enzyme protecting functional groups per liter of detergent wash medium, and even more preferably, at least about 10 micromols of enzyme protecting functional groups per liter of detergent wash medium.

While the enzyme protecting agents employed herein include some of the same components heretofore employed as chlorine scavengers, the amount of concentration of enzyme protecting agent which imparts improved resistance to loss of enzyme activity in the detergent wash medium is preferably greater than that required to scavenge chlorine. That is to say that such use is an improvement over such previous uses of chlorine scavengers insofar that when used at a higher concentration in the detergent wash medium, these scavengers additionally remove other oxidizing moieties which thereby improves the enzymatic activity degradation resistance in the detergent wash medium.

SURFACTANTS

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and lakanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Suitable surfactants for use in this invention are disclosed in British Patent Application No. 2 094 826A, the disclosure of which is incorporated herein by reference.

The surfactant is generally employed in the detergent compositions of this invention in a cleaning effective amount. Preferably, the surfactant is employed in an amount from about 1 weight percent to about 95 weight percent of the total detergent composition and more preferably from about 5 weight percent to about 45 weight percent of the total detergent composition.

In addition to the enzyme, and the coating, the detergent compositions of this invention can additionally contain the following components:

CATIONIC SURFACTANTS AND LONG-CHAIN FATTY ACID SALTS

Such cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

BUILDERS

A. Divalent sequestering agents.

The detergent composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular elecrolytes, non-dissociating polymers, salts of dicarboxylic acids, and aluminosilicate salts. Suitable divalent sequestering agents are disclosed in British Patent Application No. 2 094 826 A, the disclosure of which is incorporated herein by reference.

B. Alkalis or inorganic electrolytes

The detergent composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

ANTIREDEPOSITION AGENTS

The detergent composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose or/and polyethylene glycol with the cellulase composition of the present invention provides for an especially useful dirt removing composition.

For removing the decomposition of carboxymethylcellulose by the cellulase in the detergent, it is desirable that carboxymethylcellulose is granulated or coated before the incorporation in the composition.

BLEACHING AGENTS

The use of certain enzymes, e.g., cellulase, in combination with a bleaching agent such as sodium percarbonate, sodium perborate, sodium sulfate/hydrogen peroxide adduct and sodium chloride/hydrogen peroxide adduct or/and a photosensitive bleaching dye such as zinc or aluminum salt of sulfonated phthalocyanine further improves the deterging effects.

BLUING AGENTS AND FLUORESCENT DYES

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

CAKING INHIBITORS

The following caking inhibitors may be incorporated in the powdery detergent: p-toluenesulfonic acid salts, xylenesulfonic acid salts, acetic acid salts, sulfosuccinic acid salts, talc, finely pulverized silica, clay, calcium silicate (such as Micro-Cell of Johns Manville Co.), calcium carbonate and magnesium oxide.

MASKING AGENTS FOR FACTORS INHIBITING THE CELLULASE ACTIVITY

Certain enzymes, e.g., cellulase are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

In regard to the enzymes, certain components can act as inhibitors. For example, with cellulase, it is known that cellobiose, glucose and gluconolactone act sometimes as the inhibitors. It is preferred to avoid the co-presence of these inhibitors with the enzyme as far as possible. In the event that co-presence is unavoidable, it is necessary to avoid the direct contact of the inhibitors with the enzyme by, for example, coating them.

Long-chain-fatty acid salts and cationic surfactants can act as the inhibitors of some enzymes, e.g., cellulase, in some cases. However, the co-presence of these substances with the enzyme is allowable if the direct contact of them is prevented by some means such as tableting or coating.

The above-mentioned masking agents and methods may be employed, if necessary, in the present invention.

ENZYME-ACTIVATORS

Certain enzymes, e.g. cellulase, are known to be activated by the presence of materials referred to as activators. For cellulase, the activators vary depending on variety of the cellulases. In the presence of proteins, cobalt and its salts, magnesium and its salts, and calcium and its salts, potassium and its salts, sodium and its salts or monosaccharides such as mannose and xylose, the cellulases are activated and their degerging powers are improved remarkably.

ANTIOXIDANTS

The antioxidants include, for example, tert-butylhydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

SOLUBILIZERS

The solubilizers include, for example, lower alcohols such as ethanol, benzensulfonate salts, lower alkylbenzensulfonate salts such as p-toluenesulfonate salts, glycols such as propylene glycol, acetylbenzenesulfonate salts, acetamides, pyridinedicarboxylic acid amides, benzoate salts and urea.

The detergent composition of the present invention can be used in a broad pH range of from acidic to alkaline pH. Preferably, the detergent composition is employed in a neutral/alkaline pH and more preferably in a neutral/alkaline pH of from pH 7 to 10.

Aside from the above ingredients, perfumes, buffers, preservatives, dyes and the like can be used, if desired, with the detergent compositions of this invention.

When the detergent composition is added to an aqueous solution so as to produce a cleaning effective concentration of a surface active agent, the resulting aqueous solution is sometimes referred to herein as a "detergent wash medium".

When a detergent base used in the present invention is in the form of a powder, it may be one which is prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. The granules have a size of from 50 to 2000 micrometers. After the spray-drying, perfumes, enzymes, bleaching agents, inorganic alkaline builders may be added. With a highly dense, granular detergent base obtained such as by the spray-drying-granulation method, various ingredients may also be added after the preparation of the base.

The following examples are representative and not intended to be limiting. One skilled in the art could choose other enzymes, cores, particles, methods and coating agents based on the proportions and ingredients taught herein.

The following examples were prepared using techniques similar to those described in co-pending U.S. application Ser. No. 07/429,881 incorporated herein by reference as a spray-coating. The following example procedure used for all the examples.

EXAMPLE 1

A Uni-Glatt laboratory fluidized-bed spray-coater was charged with 1210 grams of non pareils cores or seeds having a diameter of 425 to 850 microns. A 1.05 liter aqueous cellulase concentrate (cellulase available as Cytolase 123 from Genencor International, 180 Kimball Way, South San Francisco, Calif. 94080) containing 170 grams/liter protein and 25% total solids was sprayed onto the fluidized cores at a spray rate of about 10 ml/min with an inlet temperature of 45° to 62° C. and an outlet temperature of 38° to 46° C. At the end of the enzyme application, 1466 grams of granules were recovered, representing a 21.2% weight gain over the non pareil core. The resulting granules were screened to provide granules between 425 and 1180 microns, a total of 1411 grams. The recovery of protein in the 425 and 1180 microns granules was 87.0% of the protein occurring in the cellulase concentrate applied. The protein content of these granules was determined to be 110 grams/kilogram. These granules are hereinafter referred to as "Granule A".

Granule A (706 grams) was then charged into a Uni-Glatt fluidized-bed-spray-coater and coated with 37 grams of ammonium sulfate dissolved in 100 mls final volume of deionized water. The ammonium sulfate solution was sprayed onto the fluidized granules at around 10 mls/min with an inlet temperature of 50° to 60° C. and an outlet temperature of 40° to 45° C. Subsequently, a solution containing 15% AQ-55 polymer solids and 15% suspended titanium dioxide was spray-coated onto the granule in a similar fashion, and enough was applied to result in 4% net dry weight percentage of each $TiO_2$ and AQ-55. These granules were screened to provide granules between 425 and 1180 microns, a total of 727 grams. The recovery of protein in the granules between 425 to 1180 microns was 98.1% of the protein occurring in the Granule A material charged into the fluidizied-bed spray-coater. The protein content of these granules was determined to be 105 grams/-kilogram. These granules are hereinafter referred to as "Granule B".

A fully formulated commercially available powdered laundry detergent was separately formulated into two separate compositions. The first composition contained a sufficient amount of Granule A so as to provide 0.1 weight percent of cellulase (hereinafter "Composition A"); whereas the second composition contained a sufficient amount of Granule B so as to provide the same weight percent of cellulase (hereinafter "Composition B"). The same amount of Composition A and Composition B were added to separate washing machines each of which contained 17 gallons of water at 37° C. Immediately after addition, a 20 ml aliquot of each solution was withdrawn and the enzymatic activity was measured, i.e., the zero point measurement. Additional aliquots were withdrawn at 3 minute intervals and the activity was measured for these samples as well.

EXAMPLE 2

The following results were achieved by varying the general amounts of coating and protecting agents.

By a similar method to that described in Example 1, a series of samples of spray-coated subtilisin were produced incorporating varying levels of ammonium sulfate and AQ-55 polymer. In all samples, the following procedure was approximately constant: A Uni-Glatt laboratory fluidized-bed spray-coater was charged with 600 and 950 grams of non pareil seeds having a diameter of 425 to 850 microns. The weight of non pareils was varied based on the desired target concentrations of ammonium sulfate and AQ-55 polymer to be added, in order to achieve an approximately constant final product weight and enzyme concentration. An enzyme concentrate containing from 10 to 20% w/v total solids and a subtilisin concentration of from 1.0 to 3.0% w/v was sprayed onto the fluidized seeds at a rate of about 10 ml/min and an atomization air pressure of 3.5 bar, with an inlet temperature of 45° C. to 62° C. and an outlet temperature of 34° C. to 48° C. Enough of an aqueous solution of ammonium sulfate at a 40% w/v concentration was sprayed on to provide the net dry weight percentage indicated in the table below for each sample. An aqueous suspension was prepared containing 15% AQ-55 polymer solids and 15% suspended titanium dioxide, and enough was applied to provide the net dry weight percentage of AQ-55 indicated in Table 1 (i.e., titanium dioxide is present at an equal proportion as the polymer). Final produce, at approximately 1000 to 1100 grams weight, was harvested from the fluidized bed, and screened between 16 and 50 mesh screens to remove fines and agglomerates.

The ten samples prepared had polymer and ammonium sulfate compositions indicated by the non-empty cells in Table 1. (The combinations represented by the empty cells were not produced or tested). These samples were then tested for wash performance in washing machines, using a proprietary detergent in a 12 minute cycle at 95° F. Standard stain swatches were evaluated for cleaning benefit by single-blind subjective tests and assigned a relative rating. In the following table, performance ratings are scaled between 0.0 and 2.0, with a higher rating representing a subjectively cleaner swatch.

TABLE 1

Cleaning Performance of Detergent Protease Granules Coated the Ammonium Sulfate and AQ-55 Polymer

| Percent | Percent Ammonium Sulfate | | | |
|---|---|---|---|---|
| AQ-55 Polymer | 0 | 5 | 10 | 15 |
| 0 | | | | 0.3 |
| 2 | | 0.7 | 1.2 | |
| 3 | | | 1.6 | |
| 4 | 0.5 | 1.0 | 1.5 | 1.8 |
| 6 | | 1.2 | 1.5 | |

The swatch cleaning ratings on Table 1 indicate an additive performance benefit for combinations of increased polymer levels and increased ammonium sulfate levels. Thus, it is apparent that good cleaning performance can be maintained at low levels of chlorine scavenger by compensating with increased levels of AQ-55 polymer.

We claim:

1. A particulate enzyme containing material coated with a continuous layer capable of delaying the release of at least a portion of the particulate enzyme containing material in aqueous solutions, said layer comprising a non-water soluble isophthalic acid polymer.

2. A particulate material according to claim 1 further comprising a detergent.

3. A particulate material according to claim 1 wherein the isophthalic acid polymer is poly [82/18-isophthalic acid/5-sodiosulfonoisophthalic acid 54/46 diethyleneglycol/1,4-cyclohexane dimethanol].

4. A particulate material according to claim 1 further comprising an enzyme protecting agent, masking agent or pigment.

5. A particulate material according to claim 4 wherein the pigment is $TiO_2$.

6. A particulate material according to claim 4 wherein the enzyme protecting agent is ammonium sulfate.

7. A particulate material according to claim 1 wherein the polymer is crosslinked with multivalent cation salts.

8. A particulate material according to claim 7 wherein the multivalent cation salt is aluminum sulfate.

* * * * *

UNITED STATES PATENT AND TRADEMARK OFFICE

CERTIFICATE OF CORRECTION

PATENT NO. : 5,254,283

DATED : October 19, 1993

INVENTOR(S) : Raymond E. Arnold, Nathaniel T. Becker

It is certified that error appears in the above-indentified patent and that said Letters Patent is hereby corrected as shown below:

On the title page, item [75]:

Add Inventors: Richard P. Crowley, Rochester, New York
Ernest P. Smith, Blountville, Tennessee Signed and Sealed this Ninth Day of May, 1995

Attest:

BRUCE LEHMAN

*Attesting Officer* *Commissioner of Patents and Trademarks*